US006664397B1

(12) United States Patent
Fletcher et al.

(10) Patent No.: US 6,664,397 B1
(45) Date of Patent: Dec. 16, 2003

(54) USE OF (+)MEFLOQUINE FOR THE TREATMENT OF MALARIA (75) Inventors: Allan Fletcher, Cleveland (GB); Robin Shepherd, deceased, late of Berkshire (GB), by Joy Miriam Shepherd, legal representative (73) Assignee: Vernalis Research Limited, Winnersh (GB)

(*) Notice: Subject to any disclaimer, the term of this patent is extended or adjusted under 35 U.S.C. 154(b) by 0 days.

(21) Appl. No.: 09/380,353

(22) PCT Filed: Mar. 6, 1998

(86) PCT No.: PCT/GB98/00675

§ 371 (c)(1),
(2), (4) Date: Nov. 22, 1999

(87) PCT Pub. No.: WO98/39003

PCT Pub. Date: Sep. 11, 1998

(30) Foreign Application Priority Data

| Mar. 7, 1997 | (GB) | 9704809 |
| Oct. 21, 1997 | (GB) | 9722232 |
| Nov. 17, 1997 | (GB) | 9724263 |
| Nov. 21, 1997 | (GB) | 9724712 |

(51) Int. Cl.$^7$ .................... A61K 31/47; C07D 215/00; C07D 215/12
(52) U.S. Cl. .................. 546/314; 514/895; 546/152; 546/176
(58) Field of Search .............. 546/176, 152; 514/895, 314

(56) References Cited

U.S. PATENT DOCUMENTS

| 3,536,809 A | 10/1970 | Applezweig | 424/28 |
| 3,598,123 A | 8/1971 | Zaffaroni | 128/268 |
| 3,630,200 A | 12/1971 | Higuchi | 128/260 |
| 3,845,770 A | 11/1974 | Theeuwes et al. | 128/260 |
| 3,916,899 A | 11/1975 | Theeuwes et al. | 128/260 |
| 4,008,719 A | 2/1977 | Theeuwes et al. | 128/260 |
| 4,327,215 A | 4/1982 | Hickmann et al. | 546/176 |
| 4,687,660 A | 8/1987 | Baker et al. | 424/465 |
| 4,769,027 A | 9/1988 | Baker et al. | 424/493 |

OTHER PUBLICATIONS

Peters, et al., "The Chemotherapy of Rodent Malaria. Response of Plasmodium Yoelii ssp. NS to Mefloquine and its Enantiomers", *Ann. Trop. Med. Parasitol.*, 89:5 465–468 (1995).
Karle, et al., "Plasmodium Falciparum: Role of Absolute Stereochemistry in the Antimalarial Activity of Synthetic Amino Alcohol Antimalarial Agents", *Exp. Parasitol.*, 176:4 345–351 (1993).
Vidrequin, et al., "Uptake of Melfliquine Enantiomers into Uninfected and Malaria–infected Erythrocytes", *Drug Metab. Dispos.*, 24:6 689–691 (1996).

P.D. Theisen et al., "J. Org. Chem." 53, Improved Procedure for Preparation of Optically Active 3–Hydroxyglutarate Monoesters and 3–Hydroxy–5–oxoalkanoic Acids, pp. 2374–2378, (1988).
W. Peters et al., "Annals of Tropical Medicine and Parasitology" vol. 89 No. 5, The chemotherapy of rodent malaria. LII. Response of *Plasmodium yoelii* ssp. NS to mefloquine and its enantiomers, pp. 465–468, (1995).
S.M. Poucher et al., "British Journal of Pharmacology" 115, The in vitro pharmacology of ZM 241385, a potent, non–xanthine, $A_{2a}$ selective adenosine receptor antagonist, pp. 1096–1102, (1995).
J. Shimada et al., "Bioorganic & Medicinal Chemistry Letters" vol. 7 No. 18, Adenosine $A_{2a}$ Antagonists with Potent Anti–Cataleptic Activity, pp. 2349–2352, (1977).
R.M. Pinder et al., "Antimalarials." II, Antimalarials. II.$^{1a}$ α–(2–Piperidyl)– and α–(2–Pyridyl)–2 trifluoromethyl–4–quinolinemethanols$^{1b}$, pp. 267–269, (Mar. 1968).
WHO Scientific Group, "Practical chemotherapy of malaria", (1990).
K.J. Palmer et al., "Drugs" 45 (3), Mefloquine, pp. 430–475, (1993).
T.A. Ruff et al., "The Medical Journal of Australia" vol. 161, Seizure associated with mefloquine for malaria prophylaxis, pp. 452–453, (1994).
"British Medical Journal" vol. 313, pp. 524–529, (Aug. 31, 1996).
L.K. Basco et al., "Br. J. clin. Pharmac." 33, In vitro activity of the enantiomers of mefloquine, halofantrine and enpiroline against *Plasmodium falciparum*, pp. 517–520, (1992).
C.Hennequin et al., "Arch Intern Med" vol 154, Severe Psychiatric Side Effects Observed During Prophylaxis and Treatment with Mefloquine, pp. 2360–2362, (Oct. 24, 1994).
A. Sowunmi et al., "Transactions of the Royal Society of Tropical Medicine and Hygiene" vol. 87, Neuropsychiatric side effects of mefloquine in Africans, pp. 462–463, (1993).
G.M. Gullahorn et al., "The Lancet" vol 341, Anaesthesia emergence delirium after mefloquine prophylaxis, pp. 632–633, (Mar. 6, 1993).

(List continued on next page.)

Primary Examiner—Alan L. Rotman
Assistant Examiner—Raymond Covington
(74) Attorney, Agent, or Firm—Foley & Lardner (57) ABSTRACT

Use of (+)-(11R,2'S)-α-2-piperidinyl-2,8-bis (trifluoromethyl)-4-quinolinemethanol or a pharmaceutically acceptable salt thereof substantially free of its (−)-enantiomer in the manufacture of a medicament having reduced side-effect compared to the racemic (±)-(R*,S*)-α-2-piperidinyl-2,8-bis(trifluoromethyl)-4-quinolinemethanol for treating or preventing malaria in a subject. A method of treating or preventing malaria with reduced side-effects comprising administration of (+)-(11R,2'S)-α-2-piperidinyl-2,8-bis(trifluoromethyl)-4-quinolinemethanol or a pharmaceutically acceptable salt thereof substantially free of its (−)-enantiomer.

31 Claims, 3 Drawing Sheets

OTHER PUBLICATIONS

A.M.J. Croft et al., "The Lancet" vol 347, Neuropsychiatric reactions with mefloquine chemoprophylaxis, pp. 326–327, (Feb. 3, 1996).

F.I. Carroll et al., "Journal of Medicinal Chemistry" vol 17 No. 2, Optical Isomers of Aryl–2–piperidylmethanol Antimalarial Agents, Preparation, Optical Purity, and Absolute Stereochemistry, pp. 210–219, (1974).

C.J. Ohnmacht et al., "Journal of Medicinal Chemistry" vol 14 No. 10, Antimalarials. 7. Bis(trifluoromethyl)–α–(2–piperidyl)–4–quinolinemethanols[1], pp. 926–929, (1971).

J.M. Karle et al., "Exp. Parasitol" 76, *Plasmodium falciparum:*, Role of Absolute Stereochemistry in the Antimalarial Activity of Synthetic Amino Alcohol Antimalarial Agents, pp. 345–351, (1993).

C. Ledent et al., "Nature" vol. 388, Aggressiveness, hypoalgesia and high blood pressure in mice lacking the adenosine $A_{2a}$ receptor, pp. 674–679, (Aug. 14, 1997).

K. A. Jacobson et al., "Purinergic Approaches in Experimental Therapeutics" chap. 6, Development of Selective Purinoceptor Agonists and Antagonists, pp. 102–128, (1997).

R. Speich et al., "The New England Journal of Medicine" vol. 331, No. 1, Central Anticholinergic Syndrome with the Animalarial Drug Mefloquine, pp. 57–58, (Jul. 7, 1994).

Nai–Shin Chu, "Epilepsia" 22, Caffeine– and Aminophylline–Induced Seizures, pp. 85–94, (1981).

L.J.S. Knutsen et al., "Purinegic Approaches in Experimental Therapeutics" chap. 22, Adenosine and ATP in Epilepsy, pp. 423–447, (1997).

K.A.Rudolphi et al., "Journal of Cerebral Blood Flow and Metabolism" 7, Effect of Theophylline on Ischemically Induced Hippocampal Damage in Mongolian Gerbils: A Behavioral and Histopathological Study, pp. 74–81, (1987).

- Control (NECA)
- (−) enantiomer
- (+) enantiomer

FIG. 6

- CGS21680
- CGS+1 μM (−) enantiomer
- CGS+1 μM (+) enantiomer

USE OF (+)MEFLOQUINE FOR THE TREATMENT OF MALARIA

The present invention relates to the use of an enantiomer of α-2-piperidinyl-2,8-bis(trifluoromethyl)-4-quinolinemethanol (mefloquine) as an anti-malarial.

Malaria is an infectious parasitic disease transmitted by mosquitoes. It is characterized by periodic fever and an enlarged spleen. Malaria affects some 200 million people a year. Malaria in humans is caused by 4 species of parasitic protozoa belonging to the genus Plasmodium. Of these, *P. falciparum* produces the severe disease while *P. malariae, P. vivax* and *P. ovale* cause milder forms.

Malaria is transmitted by infected female Anopheline mosquitoes. The Plasmodia parasite matures in the insect, and is then transferred when the mosquito bites a human. Inside the human, the parasite settles first in the liver, multiplies and then invades the red blood cells. This is when the symptoms of malaria become evident.

Despite numerous attempts at eradication, malaria remains a serious endemic disease in many areas of Africa, Latin America and Oceania, with a worldwide mortality rate of approximately 1 million per year (WHO Scientific Group on the Chemotherapy of Malaria 1990). One of the major factors contributing to the continued presence of malaria is the emergence of malaria parasites that are resistant to one or more anti-malarial compounds.

Mefloquine is an anti-malarial compound which is effective against strains of the Plasmodium parasite which have developed resistance to conventional anti-malarial agents (for a review of its antimalarial activity, pharmacokinetic properties and therapeutic efficacy, see Palmer et al, Drugs, 1993, 45, 430–475). However, mefloquine resistance has now been reported in a number of areas including areas of Thailand (see Palmer et al.). Nevertheless, mefloquine is still one of the most effective anti-malarial mono-therapies and its use has increased greatly. Recently, the drug has attracted considerable adverse publicity owing to the incidence of severe neuropsychiatric side-effects, e.g. depression, psychosis, panic attacks, generalised anxiety. Although central nervous system (CNS) side-effects had been reported previously (particularly from its use by the armed forces in tropical areas; Croft & World (Neuropsychiatric reactions with mefloquine chemoprophylaxis. Lancet, 1996, 347, 326); Gullahorn et al. (Anaesthesia emergence delerium after mefloauine prophylaxis. Lancet, 1993, 341, 632)), their incidence had been regarded as sufficiently low to be of little concern. However, the widespread use of the drug by holidaymakers has resulted in a greatly increased number of CNS side-effect reports. A recent study (Barrett et al. (Comparison of adverse events associated with use of mefloquine and combination of chloroquine and proguanil as antimalarial prophylaxis: postal and telephone survey of travellers. (British Medical Journal, 1996, 313, 525–528), in which 3851 travellers taking prophylactic anti-malarial medication were surveyed, has confirmed that there is a significant excess of adverse neuropsychiatric events associated with mefloquine administration compared with an alternative prophylactic treatment (proguanil plus chloroquine).

Clinical reports indicate that mefloquine may be proconvulsant (Ruff et al. (Seizure associated with mefloquine for malaria prophylaxis. Med. J. Aust., 1994, 161, 453)), anxiogenic (Hennequin et al. (Severe psychiatric side effects observed during prophylaxis and treatment with mefloquine. Arch. Intern. Med., 1994, 154, 2360–2362)), induce vertigo and dizziness (Sowunmi et al. (Neuropsychiatric side effects of mefloquine in Africans. Trans. Roy. Soc. Trop. Med. Hyg., 1993, 87, 462–463)) and may have central anticholinergic actions (Speich and Heller (Central anticholinergic syndrome with the antimalarial drug mefloquine. N. Engl. J. Med., 1994, 331, 57–58)).

Mefloquine is a molecule having two asymmetric carbon atoms and is usually used clinically as a racemic mixture of erythro ((±) (R*,S*)) isomers. Both of the mefloquine enantiomers have been reported to be equally effective against *Plasmodium falciparum* (Basco et al. (In vitro activity of the enantiomers of mefioquine, halofantrine and enpiroline against *Plasmodium falciparum*. Br. J. clin. Pharmac., 1992, 33, 517–520)), although another study claimed that the (+)-enantiomer was more potent than the (−)-enantiomer by a factor of 1.69–1.81 (Karle et al. (*Plasmodium falciparum*: role of absolute stereochemistry in the antimalarial activity of synthetic amino alcohol antimalarial agents. Exp. Parasitol., 1993, 76, 345–351)).

Mefloquine hydrochloride was introduced to the market as an anti-malarial agent in 1985. There have been over 40 families of patent applications on mefloquine covering: the use of the compound for treating malaria and other parasitic diseases; various processes for its preparation; and different formulations. The compound and its preparation was first described by Ohnmacht et al. (*J. Med. Chem.* 1971, 14, 926) in 1971. A more detailed account of the stereochemistry, synthesis, and anti-malarial activity of the isomers of mefloquine is given by Carroll and Blackwell (*J. Med. Chem.* 1974, 17, 210–219) in 1974.

It has now been found that the (+)-(11R,2'S)-enantiomer of α-2-piperidinyl-2,8-bis(trifluoromethyl)-4-quinolinemethanol is effective as an anti-malarial and has reduced side-effects compared to the racemic (±)-(R*,S*)-α-2-piperidinyl-2,8-bis(trifluoromethyl)-4-quinolinemethanol. The structures of the (+)-(11R,2'S)-enantiomer and the (−)-(11S,2'R)-enantiomer of α-2-piperidinyl-2,8-bis(trifluoromethyl)-4-quinolinemethanol are shown below.

(+)-enantiomer
(+)-(11R, 2'S)

(−)-enantiomer
(−)-(11S, 2'R)

In particular, it has been found that the (−)-enantiomer of mefloquine binds to CNS adenosine receptors, while the (+)-enantiomer is without significant activity at this binding site. The blocking of central adenosine receptors by the (−)-enantiomer is believed to result in the neuropsychiatric symptoms associated with mefloquine.

According to the present invention there is provided use of (+)-(11R,2'S)-α-2-piperidinyl-2,8-bis(trifluoromethyl)-4-quinolinemethanol or a pharmaceutically acceptable salt thereof substantially free of its (−)-enantiomer in the manufacture of a medicament having reduced side-effects compared to the racemic (±)-(R*,S*)-α-2-piperidinyl-2,8-bis(trifluoromethyl)-4-quinolinemethanol for treating or preventing malaria.

According to a further aspect of the present invention there is provided a method of treating or preventing malaria with reduced side-effects compared to the racemic (±)-(R*,S*)-α-2-piperidinyl-2,8-bis(trifluoromethyl)-4-quinolinemethanol comprising administration to a subject in need of such treatment an effective dose of (+)-(11R,2'S)-α-2-piperidinyl-2,8-bis(trifluoromethyl)-4-quinolinemethanol or a pharmaceutically acceptable salt thereof substantially free of its (−)-enantiomer.

The present invention may be employed in respect of a human or animal subject, more preferably a mammal, more preferably a human subject.

(+)-(11R,2'S)-α-2-piperidinyl-2,8-bis(trifluoromethyl)-4-quinolinemethanol may be employed in the present invention in an admixture with one or more other anti-malarial drugs such as, for example, chloroquine, pyrimethamine, sulfadoxine, amodiaquine, quinine/quinidine, halofantrine, artemether/artesunate, tovaquone, proguanil, doxycycline and dapsone. Combination with pyrimethamine and sulfadoxine is particularly preferred. According to a further aspect of the invention, (+)-(11R,2'S)-α-2-piperidinyl-2,8-bis(trifluoromethyl)-4-quinolinemethanol and the other anti-malarial drug(s) may be in separate formulations, for use simultaneously or sequentially.

The term "a method for treating or preventing malaria" as used herein, means relief from malaria, preventing or inhibiting infection by parasitic protozoa of the genus Plasmodium which cause malaria and clearance of parasitic protozoa.

The term "substantially free of its (−)-enantiomer", as used herein, means that the composition contains a greater proportion of (+)-(11R,2'S)-α-2-piperidinyl-2,8-bis(trifluoromethyl)-4-quinolinemethanol in relation to (−)-(11S,2'R)-α-2-piperidinyl-2,8-bis(trifluoromethyl)-4-quinolinemethanol. In a preferred embodiment of the present invention the term "substantially free of its (−)-enantiomer" as used herein means that the composition contains at least 90% by weight of (+)-(11R,2'S)-α-2-piperidinyl-2,8-bis(trifluoromethyl)-4-quinolinemethanol and 10% by weight or less of (−)-(11S,2'R)-α-2-piperidinyl-2,8-bis(trifluoromethyl)-4-quinolinemethanol. In a further preferred embodiment, the term "substantially free of its (−)-enantiomer" means that the composition contains at least 99% by weight of (+)-(11R,2'S)-α-2-piperidinyl-2,8-bis(trifluoromethyl)-4-quinolinemethanol and 1% or less of (−)-(11S,2'R)-α-2-piperidinyl-2,8-bis(trifluoromethyl)-4-quinolinemethanol. In another preferred embodiment, the term "substantially free of its (−)-enantiomer" as used herein means that the composition contains 100% by weight of (+)-(11R,2'S)-α-2-piperidinyl-2,8-bis(trifluoromethyl)-4-quinolinemethanol. The above percentages are based on the total amount of α-2-piperidinyl-2,8-bis(trifluoromethyl)-4-quinolinemethanol present in the composition.

The term "reduced side-effects", as used herein, means that the pharmaceutical compositions employed in the present invention allow treatment and prevention of malaria and cause less side-effects than the racemic (±)-(R*,S*)-α-2-piperidinyl-2,8-bis(trifluoromethyl)-4-quinolinemethanol. In a preferred embodiment of the present invention the term "reduced side effects", as used herein, means that the pharmaceutical compositions employed in the present invention allow treatment and prevention of malaria and cause substantially less side-effects than the racemic (±)-(R*,S*)-α-2-piperidinyl-2,8-bis(trifluoromethyl)-4-quinolinemethanol. In a more preferred embodiment of the present invention the term "reduced side-effects", as used herein, means that the pharmaceutical composition employed in the present invention allow treatment and prevention of malaria and cause substantially no side-effects. The side-effects that are reduced, preferably substantially reduced, and more preferably avoided, include neuropsychiatric side-effects such as depression, psychosis, irritability, aggressiveness, panic attacks and generalised anxiety; seizures; proconvulsant effects; agitation effects; vertigo; dizziness; and anticholinergic symptoms. Preferably, the pharmaceutical compositions employed in the present invention exhibit reduced, preferably substantially reduced, preferably eliminated side effects associated with puringergic receptor binding activity.

It has been found that the (−)-enantiomer binds strongly to the adenosine receptor, while the (+)-enantiomer exhibits only a weak binding interaction.

There is evidence that blockade of adenosine receptors can result in a number of neuropsychiatric symptoms including tremor, anxiety, panic, insomnia and convulsions.

Adenosine receptors represent a sub-class ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$. Recent studies on mice bred without the adenosine $A_{2A}$ receptor (Ledent et al., (Aggressiveness, hypoalgesia and high blood pressure in mice lacking the adenosine $A_{2A}$ receptor. Nature, 1997, 388, 674–678)) indicate that these animals are more aggressive and anxious as well as having higher blood pressure than normal mice.

The effects in humans and laboratory animals of the adenosine receptor antagonists of theophylline, an asthma drug, and caffeine are well documented. These two drugs have fairly weak in vitro affinities at adenosine receptors (Ki values: theophylline $A_1$ 8.5 µM, $A_{2A}$, 25 µM; caffeine $A_1$ 29 µM, $A_{2A}$, 48 µM) (Jacobson, K. A. and van Rhee, A. M. (Development of Selective Purinoceptor Agonists and Antagonists, in Purinergic Approaches in Experimental Therapeutics, K. A. Jacobson and M. Jarvis (Eds). John Wiley and Sons, Inc., New York, 1997., pp 101–128)).

Patients taking theophylline are warned that they should inform their physicians if they have a seizure disorder, which is not surprising in view of the seizure inducing potential of adenosine receptor antagonists. Overdose with xanthines can result in seizures that are particularly refractory to treatment with clinically useful anticonvulsants (Chu, C. K. (Caffeine and aminophylline induced seizures. *Epilepsia* 1981, 22, 85–94)).

Adenosine is thought to be the agent that causes seizure arrest in man (Knutsen, L. J. S. and Murray, T. Adenosine and ATP in Epilepsy. In "Purinergic Approaches in Experimental Therapeutics", K. A. Jacobson and M. Jarvis (Eds)., John Wiley and Sons, Inc., New York, 1997, pp 423–447), and experimental data from rodents indicates that blockade of adenosine $A_1$ receptors by theophylline immediately prior to an ischaemic episode exacerbates neuronal damage (Rudolphi, K. A.; Keil, M.; Hinze, H. J. Effect of theophylline on ischemically induced hippocampal damage in Mongolian Gerbils:, a behavioral and histopathological study. J. Cereb. Blood Flow Metab. 1987, 7, 74–81).

Given the undesired CNS effects observed in mammals with the relatively weak adenosine receptor antagonists theophylline and caffeine documented in the scientific literature, it is undesirable to administer to normal human subjects a potent adenosine receptor antagonist.

According to the present invention the use of the (+)-enantiomer of mefloquine, substantially free of the (−)-enantiomer, is particularly preferred in the treatment of a subject who has consumed or is likely to consume any chemical compound which interacts with a purinergic receptor. Consumption of such a compound includes ingestion of such a compound in food or drink, and administration of a drug, for example for treatment or prophylaxis of a medical condition by any route of administration (such as, but not limited to, oral ingestion). Compounds which interact with purinergic receptors particularly include compounds which interact with adenosine receptors. Such compounds include caffeine, theobromine, theophylline, carbamazepine, papaverine and dipyridamole; particularly caffeine, theobromine, theophylline, carbamazepine and papaverine; more particularly, caffeine, theobromine, theophylline and carbamazepine; more particularly caffeine, theobromine and theophylline; more particularly caffeine and theobromine; most particularly caffeine. Compounds which interact with purinergic receptors also include ethanol.

According to a further aspect of the present invention, the use of the (+)-enantiomer of mefloquine, substantially free of the (−)-enantiomer, is particularly preferred in the treatment of a subject having, or at risk from, a medical condition related to a disorder of purinergic receptor function. Medical conditions related to purinergic receptor activity include conditions causing or caused by an imbalance in purinergic receptor activity and conditions for which the medication causes an imbalance in purinergic receptor activity. Such medical conditions include, for example, neuropsychiatric disorders, cardiovascular disorders, digestive disorders, bronchial disorders and erectile dysfunction. Neuropsychiatric disorders of the CNS include psychiatric disorders [such as depression and anxiety disorders (such as panic disorders)], sleep disorders and seizure disorders. Cardiovascular disorders, which may be diagnosed or undiagnosed, include ischaemic heart disease, arrhythmia and related disorders, congestive heart failure and cerebrovascular disease (including transient ischaemic attacks). Subjects having cardiovascular disorders (or cardiovascular system investigations) particularly include subjects undergoing treatment with a beta-blocker drug, vasodilator or nifedipine. Subjects having digestive disorders particularly include subjects undergoing treatment with proton pump inhibitors. Bronchial disorders particularly include asthma and chronic obstructive pulmonary disease. Subjects having bronchial disorders particularly include subjects undergoing treatment with theophylline.

The pharmaceutical compositions employed in the present invention comprise (+)-(11R,2'S)-α-2-piperidinyl-2, 8-bis(trifluoromethyl)-4-quinolinemethanol as an active ingredient or a pharmaceutically acceptable salt thereof and may also contain a pharmaceutically acceptable carrier and optionally other therapeutic ingredients known to those skilled in the art, such as one or more other anti-malarial drugs such as, for example, chloroquine, pyrimethamine, sulfadoxine, amodiaquine, quinine/quinidine, halofantrine, artemether/artesunate, tovaquone, proguanil, doxycycline and dapsone. The term, "pharmaceutically acceptable salts", refers to salts prepared from pharmaceutically acceptable non-toxic acids including inorganic acids and organic acids.

Since the compound employed in the present invention is basic, salts may be prepared from pharmaceutically acceptable non-toxic acids including inorganic and organic acids. Such acids include acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

Any suitable route of administration may be employed for providing the patient with an effective dosage of (+)-(11R,2'S)-α-2-piperidinyl-2,8-bis(trifluoromethyl)-4-quinolinemethanol. For example, oral, rectal, parenteral (intravenous, intramuscular), transdermal, subcutaneous, and the like may be employed. Dosage forms include tablets, troches, dispersions, suspensions, solutions, capsules, patches, and the like. The most suitable route in any given case will depend on the severity of the condition being treated. The most preferred route of administration of the present invention is the oral route. The compositions may be conveniently presented in unit dosage form and prepared by any of the methods well known in the art of pharmacy.

In practical use, (+)-(11R,2'S)-α-2-piperidinyl-2,8-bis (trifluoromethyl)-4-quinolinemethanol can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (e.g. intravenous). In preparing the compositions for oral dosage form, any of the usual pharmaceutical media may be employed as carriers, such as, for example, water, glycols, oils, alcohols, flavouring agents, preservatives, colouring agents, and the like in the case of oral liquid preparations (such as suspensions, solutions and elixirs) or aerosols; or carriers such as starches, sugars, micro-crystalline cellulose, diluents, granulating agents, lubricants, binders, disintegrating agents, and the like may be used in the case of oral solid preparations such as, for example, powders, capsules, and tablets, with the solid oral preparations being preferred over the liquid preparations. The most preferred solid oral preparation is tablets.

Because of their ease of administration, tablets and capsules represent the most advantageous oral dosage unit form in which case solid pharmaceutical carriers are employed. If desired, tablets may be coated by standard aqueous or non-aqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; 3,630,200; 4,008,719; 4,687,660; and 4,769,027, the disclosures of which are hereby incorporated by reference.

Pharmaceutical compositions employed in the present invention suitable for oral administration may be presented as discrete units such as capsules, cachets, or tablets, or aerosol sprays each containing a predetermined amount of the active ingredient as a powder or granules, a solution or a suspension in an aqueous liquid, an oil-in-water emulsion, or a water-in-oil liquid emulsion. Such compositions may be prepared by any of the methods of pharmacy, but all methods include the step of bringing the active ingredient into association with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or moulding, optionally with one or more accessory ingredients. Compressed tablets may be prepared by compressing in a suitable machine the active ingredient in a free-flowing form such as powder or granules, optionally mixed with a binder, a lubricant, an inert diluent, and/or a surface active or dispersing agent. Moulded tablets may be made by moulding in a suitable machine a mixture of the powdered compound moistened with an inert liquid diluent.

The invention is further defined by reference to the following Figures and examples. It will be apparent to those skilled in the art that many modifications, both to materials and methods, may be practised without departing from the purpose and interest of this invention.

EXAMPLES

Preparation of 2,8-bis(Trifluoromethyl)quinoline-4-carboxylic Acid

The compound 2,8-bis(trifluoromethyl)quinoline-4-carboxylic acid was prepared by the method of Hickmann et al (U.S. Pat. No. 4,327,215).

Preparation of N-Methoxy-N-methyl-2,8-bis(trifluoromethyl)-quinoline-4-carboxamide This compound was prepared using synthetic methodology reported by Thiesen et al (*J. Org. Chem.* 1988, 53, 2374). To a suspension of 2,8-bis(trifluoromethyl)quinoline-4-carboxylic acid (12.5 g, 40.4 mmol) in $CH_2Cl_2$ (200 ml) was added 1,1'-carbonyldiimidazole (7.3 g, 45 mmol) and N,O-dimethylhydroxylamine hydrochloride (4.25 g, 45 mmol). The resulting deep red solution was stirred overnight, then poured into dilute hydrochloric acid (0.25 M, 200 ml). The organic phase was separated, and washed in turn with dilute sodium hydroxide and brine, and dried ($MgSO_4$). The solvents was evaporated to leave a viscous brown oil, which was filtered through a pad of silica gel using ethyl acetate-hexane (1:1) as eluent to give a yellowish oil, 14.3 g (98%), which solidified on standing. This material was broken up under hexane to afford the product as a tan solid, m.p. 93–95°C. $\delta_H$ (400 MHz, $CDCl_3$) 8.22 (1H, d, J=1.5 Hz), 8.16 (1H, d, J=1.8 Hz), 7.85 (1H, s), 7.73 (1H, t, J=1.2 Hz), 3.52 (3H, b s) and 3.41 (3H, bs). Analysis of this material by HPLC showed it to be >99.8% pure.

Preparation of Pyridin-2-yl-2,8-bis(trifluoromethyl)-4-quinolinemethanone

To a solution of the amide described above (10 g, 28.4 mmol) in anhydrous ether (100 ml) was added a solution of 2-pyridyl lithium (Pinder et al (*J. Med. Chem.* 1968, 11, 267)) [formed by addition of 2-bromopyridine (3.3 ml, 34.6 mmol) to a solution of butyl lithium (29.7 ml of a commercial 1.6 M solution, diluted with an equal quantity of ether) at −78°C.] at −78° C. Analysis of the reaction by TLC after 10 min showed that no starting material remained. The reaction was allowed to warm to room temperature, then poured into aqueous ammonium acetate, and extracted with ether (2×100 ml), the combined organic layers washed with brine and dried ($MgSO_4$). Filtration through a pad of silica gel using ethyl acetate-hexane (1:1) afforded 9.0 g (84%) of the crude product. This was recrystallised from isopropyl alcohol to give the product as colourless needles, identical to that described in the literature (Hickmann et al; Pinder et al; Ohnmacht et al; and Adam et al. (*Tetrahedron* 1991, 36, 7609)).

Preparation of (R*,S*)-(±)-α-2-Piperidinyl-2,8-bis(trifluoromethyl)-4-quinolinemethanol (Mefloquine)

This compound was prepared according to the literature procedure (Hickmann et al; Pinder et al; and Ohnmacht et al) to give an 85:15 mix of the erythro:threo isomers (HPLC). Recrystallisation of the crude material from acetonitrile afforded the erythro isomer as a powdery white solid in >98% purity (HPLC).

Resolution of erythro enantiomers was performed according to the known procedure (Carroll, F. I. and Blackwell, J. T., *J.Med.Chem.*, 1974, 17, 210–219).

Measurement of Convulsant or Proconvulsant Effects

Several animal seizure models are available for the screening and characterisation of convulsant, proconvulsant and anticonvulsant drugs. Most models employ a chemical convulsant to induce seizures and the convulsant effects of novel compounds are measured in terms of their ability to change the dose of convulsant required to induce a seizure response (or to alter the latency to seizure onset following a bolus dose of the convulsant) Most chemical convulsants work by blocking the neurotransmitter function of gamma-aminobutyric acid (GABA), the predominant inhibitory neurotransmitter in the mammalian brain. This can be achieved by blocking the postsynaptic action of GABA using pentylenetetrazol or bicuculline, or via a presynaptic action using a GABA synthesis inhibitor such as 3-mercaptopropionic acid, an inhibitor of glutamate decarboxylase (GAD) to decrease GABA release into the synapse.

Potentiation of Pentylenetetrazole-Induced Seizures to Assess Pro-convulsant Effects Produced by a Test Compound in Mice Seizure thresholds were determined in unrestrained animals following the insertion of an infusion cannula into a lateral tail vein. The infusion cannulas comprised lengths of polythene tubing (Portex 800/100/100/100 for mice fitted with hypodermic needles removed from their plastic Luer holders (Gillette 25G or 23G respectively).

Once inserted into the tail vein these cannulas did not require any additional attachment. The incidence of cannulas becoming dislodged during the seizures was extremely low (approximately 2% of the trials). An infusion pump was used to deliver the convulsant drug (Pentylenetetrazole, 12 mg/ml) dissolved in isotonic saline at a constant rate 0.15 ml/min (mice). The animals were placed in a transparent Perspex enclosure for observation and the times to onset of clonic and tonic seizures were measured. The criteria used to define these events were: myoclonus accompanied by abrupt loss of righting reflex (clonic) and rigid extension of the fore-limbs (tonic).

Measurement of Overt Physiological and Behavioral Effects in Mice Using the Irwin Screen Animals were weighed, coded and placed in cages, and then allowed to habituate to the environment for 20 minutes. Five animals were allocated per treatment group. Body temperature was recorded (rectally in the mouse) prior to drug administration. The compound was administered at various doses, including a vehicle control group. Treatment groups were coded so that the operator was unaware of drug or dose given.

Animals were placed in Perspex chambers for observations at 20, 60, 180 minutes after injection for a period of 10–15 minutes. If the compound was administered intravenously, animals were placed into Perspex chambers immediately after injection for observation. Body temperature and any behavioral changes were recorded.

Pilot studies were carried out initially to determine doses of compound to be used in an experiment. Only 3 animals were used per dose group. An initial low dose was administered and subsequent doses given were higher or lower depending on effects produced. Time of onset of drug action and maximum effects were also recorded.

Observations made were categorised in qualitative terms. A checklist of the behavioral and physiological signs used to assess overt effects of test compounds is shown in Table 1.

TABLE 1

Check-List of Observations for Irwin Screening

| OVERT BEHAVIOUR | AUTONOMIC OBSERVATIONS |
|---|---|
| increased activity | piloerection |
| decreased activity | diarrhoea |
| sedation | exophthalmos |
| tremor | salivation |
| convulsions | vasoconstriction |
| -myoclonic | vasodilatation |
| -tonic/clonic | cyanosis |
| straub tail | lacrymation |
| stereotypy | ptosis |
| increased exploration | miosis |
| decreased exploration | mydriasis |
| ataxia | |
| weakness | hypothermia |
| catalepsy | |
| pain threshold (tail pinch) | |
| loss of righting reflex | |
| writhing (i.p. adminstration) | |

Biological Results

The behavioral effects of the two enantiomers of mefloquine were assessed following daily dosing (30,100,300 mg/kg p.o) in mice using an Irwin Screen. Clear qualitative differences were observed between the two enantiomers, with the (−)-enantiomer appearing more potent in eliciting spontaneous seizures, irritability and aggressiveness. Twenty-four hours after the first dose, animals given 300 mg/kg of the (−)-enantiomer were difficult to handle and displayed aggression toward cage-mates. After 48 hr, the same group of animals displayed spontaneous clonic seizures, increased reactivity, and reduced body weight. Within five days, the high dose (−)-enantiomer treated animals showed reduced activity, unkempt appearance and assumed a hunched body posture. Although the latter effects were observed in animals treated with the (+)-enantiomer, these effects only became apparent after 5–6 days, and did not include seizures.

In a subsequent study to assess the possibility of a proconvulsant effect of the (−)-enantiomer, it was found that 24 hrs after a single injection of either the (+)- or (−)-enantiomer (30, 100, 300 mg/kg p.o), a dose of 300 mg/kg of the (−)-enantiomer significantly reduced the latency to onset of clonic seizures induced by infusion of the convulsant drug pentylenetetrazole (PTZ). These observations are consistent with the reported neuropsychiatric side-effects of mefloquine in humans, and indicate that the (+)-enantiomer of mefloquine has significantly reduced side-effects.

Adenosine Receptor Interaction

Figure 1:
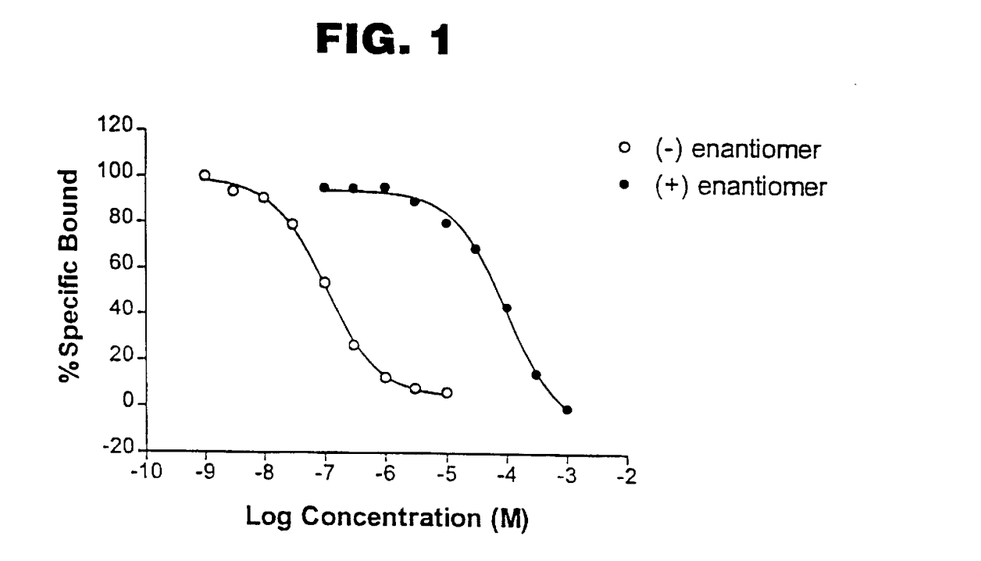
FIG. 1 shows binding of the mefloquine (+)- and (−)-enantiomers to bovine striatal adenosine receptors (non-selective) (displacement of [$^3$H]-NECA ([$^3$H]-5'-N-ethylcarboxamidoadenosine)). Table 2 displays comparative data for the control compound MECA (5'-N-methylcarboxamidoadenosine).

The mefloquine (+)- and (−)-enantiomers were initially examined separately in an assay measuring in vitro binding to adenosine receptors by determining the displacement of $[^3H]$-NECA binding to bovine striatal membranes. The data are shown in FIG. 1 and Table 2.

TABLE 2

Binding of the mefloquine (+)- and (−)-enantiomers to bovine striatal adenosine receptors (displacement of $[^3H]$-NECA). MECA is shown as control

| | Ki |
|---|---|
| MECA | 58 nM |
| (+)-enantiomer | 38 μM |
| (−)-enantiomer | 83 nM |

Figure 2:
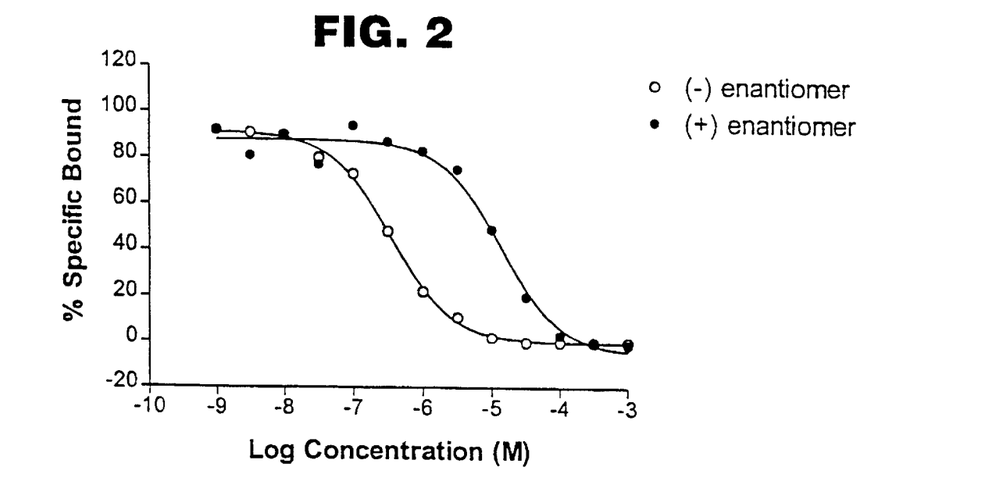
FIG. 2 shows binding of the mefloquine (+)- and (−)-enantiomers to rat brain adenosine $A_1$ receptors (displacement of [$^3$H]-DPCPX, an adenosine $A_1$ receptor antagonist).
Figure 3:
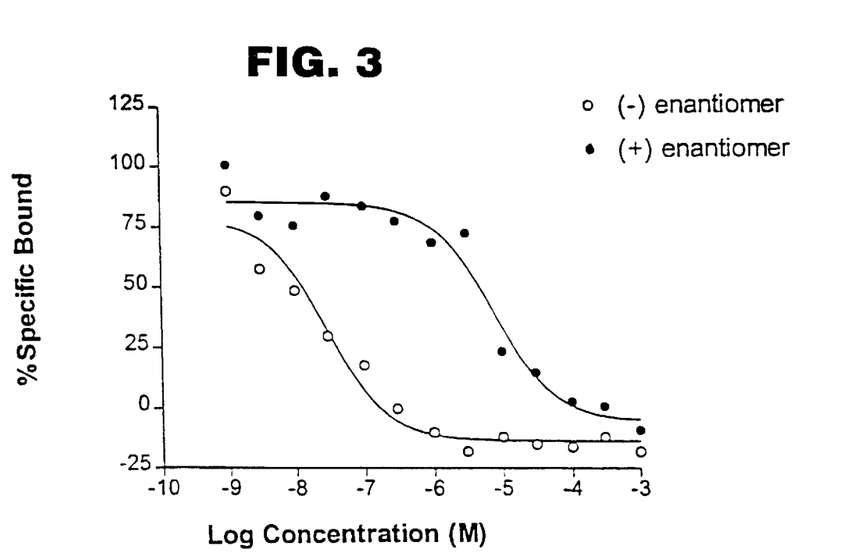
FIG. 3 shows binding of the mefloquine (+)- and (−)-enantiomers to human recombinant (HEK-293) adenosine $A_{2A}$ receptors (displacement of [$^3$H]-CGS 21680, an adenosine $A_{2A}$ receptor agonist).
Figure 4:
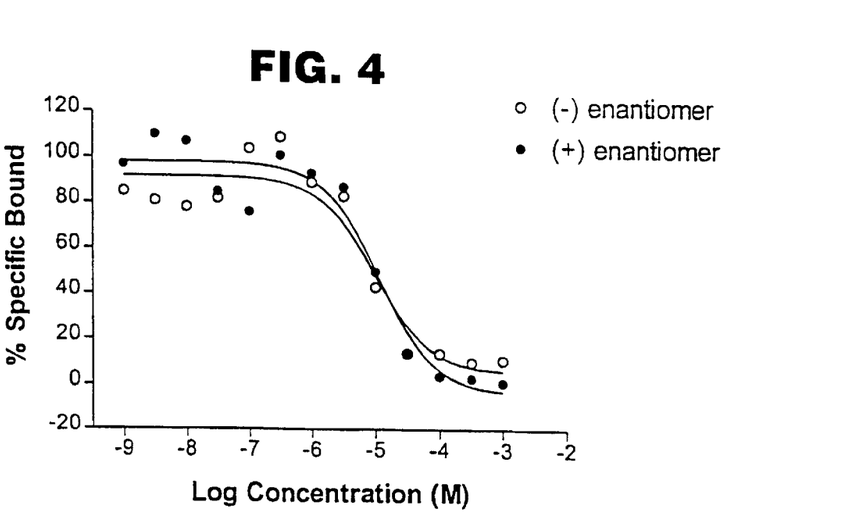
FIG. 4 shows binding of the mefloquine (+)- and (−)-enantiomers to human recombinant (HEK-293) adenosine $A_3$ receptors (displacement of [$^{125}$I]AB-MECA, an adenosine $A_3$ receptor agonist).

Once it was established that the (−)-enantiomer of mefloquine exhibited displacement of $[^3H]$-NECA in bovine striatum, the adenosine receptor subtype binding was examined using radioligand binding assays employing the selective $P_1$ radioligands $[^3H]$-DPCPX (adenosine $A_1$ receptor), $[^3H]$-CGS 21680 (adenosine $A_{2A}$ receptor) and $[^{125}I]$AB-MECA (adenosine $A_3$ receptor). The results are summarised in Table 3, with comparative literature data for other adenosine receptor ligands. The full dose response curves are shown in FIGS. 2–4.

TABLE 3

Binding of mefloquine (+)- and (−)-enantiomers to adenosine $A_1$, $A_{2A}$ and $A_3$ receptors
BINDING ASSAY CONDITIONS

| | Adenosine $A_1$ | Adenosine $A_{2A}$ | Adenosine $A_3$ |
|---|---|---|---|
| Source | Rat Brain | Human | Human |
| Ligand | 0.14 nM $[^3H]$-DPCPX | 4.0 nM $[^3H]$-CGS 21680 | 0.4 nM $[^{125}I]$AB-MECA |
| Non-Specific | 10 μM PIA | 10 μM NECA | 10 μM NECA |
| RESULTS (Ki) | | | |
| (+) enantiomer | 6.4 μM | 1.8 μM | 7.7 μM |
| (−) enantiomer | 202 nM | 4.4 nM | 6.8 μM |
| Reference Adenosine receptor agonists | | | |
| NECA | 17 nM | 19 nM | 110 nM |
| CHA | 26 nM | 510 nM | 7700 nM |
| Reference Adenosine $A_{2A}$ receptor antagonists | | | |
| KW-6002† | 580 nM | 13 nM | na |
| KF17837† | 390 nM | 8 nM | na |
| ZM241385‡ | 2.0 μM | 0.3 nM | 151 μM |

†Shimada et al., BioMed. Chem. Lett., 1997, 7, 2349–2352.
‡Poucher et al., Br. J. Pharm., 1995, 115: 1096–1102

The above data lead to the conclusion that the mefloquine (−)-enantiomer is a selective ligand for the adenosine $A_{2A}$ receptor subtype in vitro. The binding of the (+)-enantiomer is over two orders of magnitude weaker.

Assessment of the Interaction of the (+)-Enantiomer and the (−)-Enantiomer With NECA in PC-12 Cells PC-12 cells (purchased from ECACC) were maintained in RPMI 1640 media (Sigma) supplemented with 2 mM L-glutamine and 10% FCS in a controlled environment of 5% $CO_2$, 95% humidity at 37° C.

On the day of the assay the cells were gently harvested and centrifuged at 700 RPM for 10 min. The supernatant was discarded and the pellet re-suspended to a final density of approx. $1\times10^6$ cells/ml in modified RPMI 1640 media. 600 μl of this suspension was mixed with 200 μl of molten agarose cell entrapment media (Molecular Devices) pre-incubated to 37° C. The cell suspension was returned to the incubator for a further 10 minutes for equilibration. 10 μl of this cell agarose suspension was spotted onto the middle of the capsule insert well and allowed to set before being placed in the sensor chambers in the cytosensor® microphysiometer. The cells were maintained on the instrument with the low buffering capacity modified RPMI 1640 media (Molecular Devices) and their base line extracellular acidification rates allowed to settle.

Agonist concentration curves were constructed by exposing the cells to increasing concentrations of agonist for a total exposure time of approximately 1 min 53 sec. Agonist concentration curves in the presence of antagonists were performed following pre-incubation of the cells to the antagonists for at least 20 min prior to agonist exposure (in the presence of the fixed antagonist concentration) Baseline acidification rates were normalised to 100%, and all responses were calculated as a % increase over normalised baseline.

All data was fitted to Log-concentration response curves to calculate half maximally effective concentrations ($EC_{50}$ values) by non-linear regression using the Graph Pad Prism software package.

Figure 5:
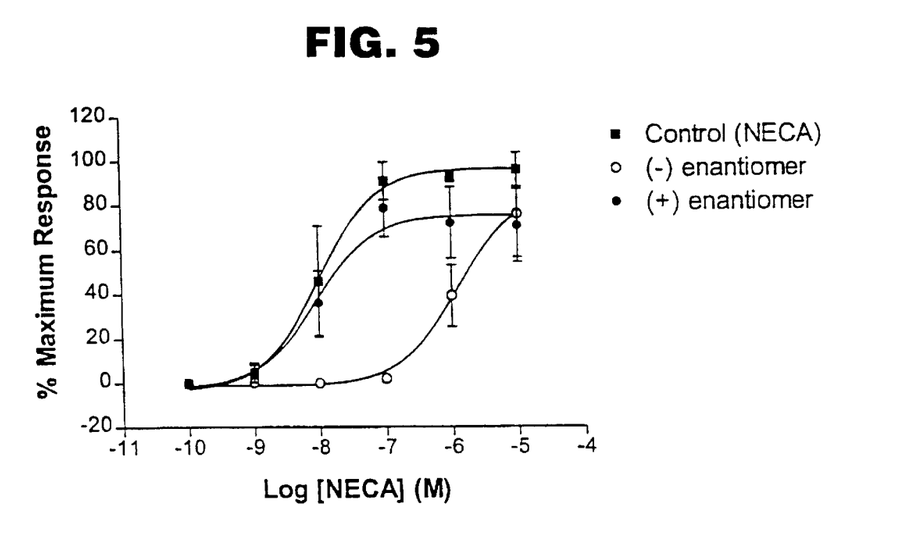
FIG. 5 shows the effect of the mefloquine (+)- and (−)-enantiomers on the NECA-induced increase in extracellular acidification rate (ECAR) in PC-12 cells.
Figure 6:
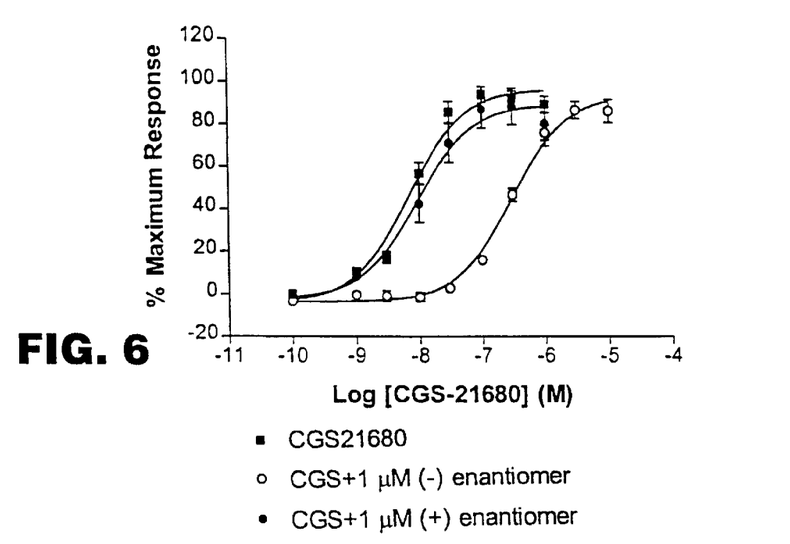
FIG. 6 shows the effect of the mefloquine (+)- and (−)-enantiomers on the CGS 21680-induced increase in ECAR in PC-12 cells.

The results (shown in FIG. 5) indicate that the (−)-enantiomer, (−)-(11S,2'R)-α-2-piperidinyl-2,8-bis(trifluoromethyl)-4-quinolinemethanol, binds to adenosine receptors as an antagonist. PC12 cells endogenously express adenosine $A_{2A}$ receptors and have been used as a source of functionally-coupled $A_{2A}$ receptors. FIG. 6 shows that similar results are obtained when CGS 21680, a selective $A_{2A}$ receptor agonist, is used instead of NECA. The antagonist effect of the (−)-enantiomer is specific to adenosine $A_{2A}$ receptors.

What is claimed is:

1. A method of treating or preventing malaria with reduced side-effects compared to the racemic (±)-(R*,S*)-α-2-piperidinyl-2,8-bis(trifluoromethyl)-4-quinolinemethanol, comprising administering to a subject in need of such treatment an effective dose of (+)-(11R,2'S)-α-2-piperidinyl-2,8-bis(trifluoromethyl)-4-quinolinemethanol or a pharmaceutically acceptable salt thereof substantially free of its (−)-enantiomer.

2. A method according to claim 1, wherein said subject is human.

3. A method according to claim 1, which further comprises administering one or more other anti-malarial drugs to said subject.

4. A method according to claim 3, wherein said anti-malarial drugs are selected from the group consisting of chloroquine, pyrimethamine, sulfadoxine, amodiaquine, quinine/quinidine, halofantrine, artemether/artesunate, tovaquone, proguanil, doxycycline and dapsone.

5. A method according to claim 1, wherein the subject is undergoing therapy with a chemical compound which interacts with purinergic receptors.

6. A method according to claim 5, wherein the subject is undergoing therapy with a drug selected from the group consisting of theobromine, theophylline, carbamazepine, papaverine or dipyridamole.

7. A method according to claim 5, wherein the subject consumes ethanol.

8. A method according to claim 2, wherein the subject has, or is at risk from, a medical condition related to a disorder of purinergic receptor function.

9. A method according to claim 8, wherein the medical condition is a neuropsychiatric disorder.

10. A method according to claim 9, wherein the medical condition is depression.

11. A method according to claim 9, wherein the medical condition is an anxiety disorder.

12. A method according to claim 11, wherein the medical condition is a panic disorder.

13. A method according to claim 9, wherein the medical condition is a sleep disorder.

14. A method according to claim 8, wherein the medical condition is a seizure disorder.

15. A method according to claim 8, wherein the medical condition is a cardiovascular disorder.

16. A method according to claim 15, wherein the medical condition is a diagnosed cardiovascular disorder.

17. A method according to claim 15, wherein the medical condition is ischaemic heart disease.

18. A method according to claim 15, wherein the medical condition is congestive heart failure.

19. A method according to claim 15, wherein the medical condition is cerebrovascular disease.

20. A method according to claim 19, wherein the medical condition is transient ischaemic attacks.

21. A method according to claim 16, wherein the subject is undergoing treatment with beta-blocker drugs.

22. A method according to claim 16, wherein the subject is undergoing treatment with a vasodilator.

23. A method according to claim 16, wherein the medical condition is arrhythmia or a related disorder.

24. A method according to claim 16, wherein the subject is undergoing treatment with nifedipine.

25. A method according to claim 8, wherein the medical condition is a digestive disorder.

26. A method according to claim 25, wherein the subject is undergoing treatment with a proton pump inhibitor.

27. A method according to claim 8, wherein the medical condition is a bronchial disorder.

28. A method according to claim 27, wherein the medical condition is asthma.

29. A method according to claim 28, wherein the subject is undergoing treatment with theophylline.

30. A method according to claim 27, wherein the medical condition is chronic obstructive pulmonary disease.

31. A method according to claim 8, wherein the medical condition is erectile dysfunction.

* * * * *